(12) United States Patent
Lopatin et al.

(10) Patent No.: US 9,448,097 B2
(45) Date of Patent: Sep. 20, 2016

(54) APPARATUS FOR DETERMINING AND/OR MONITORING A PROCESS VARIABLE OF A MEDIUM

(75) Inventors: Sergej Lopatin, Lorrach (DE); Martin Urban, Lorrach (DE)

(73) Assignee: ENDRESS + HAUSER GMBH + CO. KG, Maulburg (DE)

( * ) Notice: Subject to any disclaimer, the term of this patent is extended or adjusted under 35 U.S.C. 154(b) by 383 days.

(21) Appl. No.: 13/807,396

(22) PCT Filed: Jun. 20, 2011

(86) PCT No.: PCT/EP2011/060201
§ 371 (c)(1),
(2), (4) Date: Dec. 28, 2012

(87) PCT Pub. No.: WO2012/000814
PCT Pub. Date: Jan. 5, 2012

(65) Prior Publication Data
US 2013/0104647 A1    May 2, 2013

(30) Foreign Application Priority Data
Jul. 1, 2010   (DE) .......................... 10 2010 030 791

(51) Int. Cl.
*G01F 23/00* (2006.01)
*G01D 3/036* (2006.01)
(Continued)

(52) U.S. Cl.
CPC ............. *G01F 23/00* (2013.01); *G01D 3/0365* (2013.01); *G01F 23/2967* (2013.01); *G01K 7/32* (2013.01); *G01N 9/002* (2013.01); *G01N 11/16* (2013.01)

(58) Field of Classification Search
CPC ...................................................... G01F 23/00
USPC ........................................ 73/19.01, 292, 447
See application file for complete search history.

(56) References Cited

U.S. PATENT DOCUMENTS 4,270,123 A * 5/1981 Collard .................. G08B 17/11
340/510
5,004,906 A * 4/1991 Takasaki ................ H04N 1/407
250/214 A (Continued)

FOREIGN PATENT DOCUMENTS

CN           1469115 A       1/2004
DE       42 00 578 A1       7/1993
(Continued)

OTHER PUBLICATIONS

German Search Report in 10 2010 030 791.2, dated Jan. 19, 2011.
(Continued)

*Primary Examiner* — Hezron E Williams
*Assistant Examiner* — Tarun Sinha
(74) *Attorney, Agent, or Firm* — Bacon & Thomas, PLLC (57) ABSTRACT

An apparatus for determining and/or monitoring at least one process variable of a medium in a container which comprises a mechanically oscillatable structure, which has at least one oscillation characteristic dependent on the process variable, an electromechanical transducer having at least one piezoelectric element, which excites the structure, by means of an excitation signal supplied to the transducer, to execute mechanical oscillations, and which converts the resulting oscillations of the structure into a received signal, which corresponds to a superpositioning of the excitation signal and a wanted signal representing the oscillation. A reference element in parallel with the transducer and supplied with the excitation signal, via which a reference signal independent of the oscillation and corresponding to the excitation signal is tapped, and an electronics, which, based on the received signal and the reference signal, extracts the wanted signal, and, based on the wanted signal, determines and/or monitors the process variable, wherein, for automatic measuring of temperature of the transducer, the electronics includes a temperature measuring device, which supplies the transducer and the reference element, in temperature measurement operation, with an auxiliary signal, whose frequency lies outside a frequency range predetermined by a resonant frequency of the oscillatory structure, and, based on the wanted signal extracted in temperature measurement operation, determines a temperature of the transducer.

13 Claims, 6 Drawing Sheets

(51) Int. Cl.
*G01F 23/296* (2006.01)
*G01K 7/32* (2006.01)
*G01N 9/00* (2006.01)
*G01N 11/16* (2006.01)

(56) References Cited

U.S. PATENT DOCUMENTS

| | | | | |
|---|---|---|---|---|
| 5,073,104 A | * | 12/1991 | Kemlo | F23N 5/126 340/579 |
| 2002/0015068 A1 | * | 2/2002 | Tsukada | B41J 29/38 347/19 |
| 2003/0235233 A1 | * | 12/2003 | Kawakatsu | G01F 23/2967 374/118 |
| 2008/0015799 A1 | * | 1/2008 | Lalla | G01F 1/8409 702/65 |

FOREIGN PATENT DOCUMENTS

| | | | |
|---|---|---|---|
| DE | 43 27 167 A1 | 2/1995 | |
| DE | 197 20 519 A1 | 11/1998 | |
| DE | 10 2005 062 813 A1 | 7/2007 | |
| DE | 10 2006 007 199 A1 | 8/2007 | |
| EP | 1 376 076 A1 | 1/2004 | |
| EP | 1376076 A1 * | 1/2004 | |
| EP | 1 750 104 A2 | 2/2007 | |
| JP | 1376076 A1 * | 1/2004 | ......... G01F 23/2967 |
| WO | 02/42724 A1 | 5/2002 | |
| WO | 2012/000814 A1 | 1/2012 | |

OTHER PUBLICATIONS

International Search Report in PCT/EP2011/060201, dated Aug. 26, 2011.

International Search Report in PCT/EP2011/060201, dated Jan. 8, 2013, English translation.

* cited by examiner

APPARATUS FOR DETERMINING AND/OR MONITORING A PROCESS VARIABLE OF A MEDIUM

TECHNICAL FIELD

The invention relates to an apparatus for determining and/or monitoring at least one process variable of a medium in a container, especially a density, a viscosity or a fill level of the medium. The apparatus includes a mechanically oscillatable structure, which has at least one oscillation characteristic dependent on the process variable, an electromechanical transducer having at least one piezoelectric element, which excites the structure by means of an exciter signal supplied to the transducer to execute mechanical oscillations, and which converts the resulting oscillations of the structure into a received signal, which corresponds to a superpositioning of the exciter signal and a wanted signal representing the oscillation, a reference element supplied with the exciter signal in parallel with the transducer and via which a reference signal independent of the oscillation and corresponding to the exciter signal is tapped, and an electronics, which extracts the wanted signal based on the received signal and the reference signal, and which determines and/or monitors the process variable based on the wanted signal.

BACKGROUND DISCUSSION

Such apparatuses are applied in a large number of industrial applications, especially in measuring- and control technology and in process automation, for determining and/or monitoring the named process variables.

In the case of the most well-known apparatuses of this type, the mechanically oscillatable structure has two oscillatory fork tines coupled via a membrane, which are caused to execute oscillations of opposite phase perpendicular to their longitudinal axis via an electromechanical transducer mounted on the rear membrane side, the side facing away from the tines. Along with that, there are also apparatuses known, whose oscillatable structure is only one oscillatory rod or an oscillatable membrane.

Figure 1:
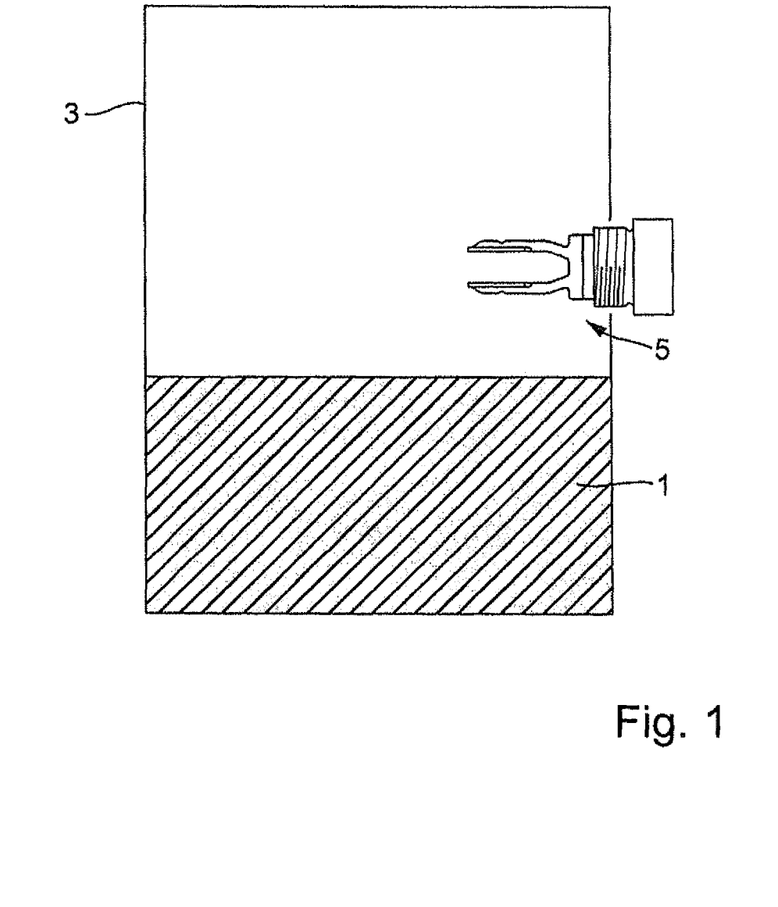
FIG. 1 is an apparatus protruding laterally into a container for monitoring a predetermined fill level.

FIG. 1 shows a classical example of a corresponding apparatus, as such is applied for monitoring a certain fill level of a medium 1 in a container 3. The mechanical, oscillatable structure 5 includes here two oscillatory rods as tines coupled via a membrane and inserted laterally into the container 3 at the height of the fill level to be monitored. The structure 5 is caused to execute oscillations, for example, via an electromechanical transducer (not shown) arranged on the rear-side of the membrane. This is done, for example, by feeding the received, oscillation reflecting signal of the transducer back to the transducer via a phase shifter and an amplifier as excitation signal. For fill-level monitoring, for example, via the phase shifter, a fixed phase shift is predetermined, by which the resonance condition for the oscillatory circuit containing the mechanical oscillatory system as frequency determining element is defined. The frequency tuned by reason of the predetermined phase shift lies in the region of the resonant frequency of the structure 5, and is subsequently generally referred to as the oscillation frequency. The oscillation frequency is measured, and compared with an earlier determined switching frequency. If it is greater than the switching frequency, then the structure 5 is oscillating freely. If it lies below the switching frequency, then the structure is covered by the medium 1, and the apparatus reports an exceeding of the predetermined fill level.

Alternatively, in the case of a perpendicular insertion of a rod- or fork shaped, oscillatable structure into the medium, with corresponding calibrating based on oscillation frequency, the degree of covering and therewith the fill level over the length of the structure can be measured.

For determining and/or monitoring density or viscosity of the medium, the structure is inserted to a predetermined immersion depth perpendicularly into the medium, and the resulting oscillation frequency, or, in the case of an exciting with a fixed excitation frequency, the amplitude or the phase shift of the resulting oscillation is measured relative to the excitation signal.

An alternative form of excitation is frequency sweep excitation, in the case of which the frequency of the excitation signal passes periodically through a predetermined frequency range. Also, here, the process variable is determined and/or monitored based on the frequency of the resulting oscillation, the amplitude of the resulting oscillation, or the phase shift of the resulting oscillation relative to the excitation signal.

Today, always more frequently, apparatuses are being applied, which have only a single electromechanical transducer having at least one piezoelectric element, which is applied both for oscillation excitement as well as also for changing the resulting oscillation into an electrical, received signal. The received signal of the transducer corresponds, in such case, to a superpositioning of the excitation signal and a wanted signal representing the oscillation. These apparatuses have, compared with apparatuses with separate transmitting- and receiving transducers, the advantage that they are clearly smaller and more cost effective to manufacture.

The excitation signal is usually a rectangular, electrical, alternating voltage. This has the result that the piezoelectric capacitance of the transducer receives a reversal of the voltage sign at the edges of the rectangular signal, whereby charging- and discharging electrical currents arise, which are superimposed as disturbance signals on an electrical current representing the mechanical oscillation.

The charging- and discharging electrical currents of the transducer are suppressed, for example, by means of a compensation capacitor. Examples of this form of disturbance signal suppression are known from DE- 197 20519A1 and EP 1 750 104A2. The apparatuses described there have, in each case, a compensation capacitor supplied with the excitation signal in parallel with the transducer. Via the compensation capacitor, a reference signal is tapped, which is independent of the oscillation and corresponds to the excitation signal. Transducer and compensation capacitor have—in the case of equal capacitance—in reference to the reverse charging events, the same behavior. If the received signal tapped via the transducer and the reference signal tapped via the compensation capacitor are, as described in DE- 197 20 519A1, subtracted from one another, or, as described in EP 1 750 104A2, added after a preceding inverting, then the disturbance signals equally contained in the two signals cancel and there is provided on the output the wanted signal reflecting the mechanical oscillations of the structure.

While the capacitance of the compensation capacitors have no, or only a very low, temperature dependence, the capacitance of the transducer is, due to the high temperature dependence of the dielectric constant of piezoelectric materials, temperature dependent in high measure. This leads to the fact that the compensation of the disturbance signals functions yet poorer, the greater the temperature related difference between the capacitance of the transducer and the capacitance of the compensation capacitor.

This problem is solved in EP 1 750 104 A2 by matching the capacitance of the compensation capacitor provided for suppressing the reverse charging peaks by controlling the voltage across the compensation capacitor as a function of the capacitance of the transducer. For this, transducer and compensation capacitor are supplied supplementally with an auxiliary signal, whose frequency lies outside the frequency range, in which the resonant frequency of the mechanically oscillatable structure lies. In this frequency range, the structure executes a forced oscillation with the frequency of the excitation signal, so that received signal and reference signal contain, in the case of agreement of the capacitances of the two, exclusively the excitation signal and the disturbance signal. A control loop is provided, which controls the compensation voltage in such a manner that the reverse charging peaks of the reference signal compensate the reverse charging peaks of the received signal of the transducer in the case of the frequency of the auxiliary signal. In this way, the temperature dependent changes of the transducer capacitance are taken into consideration and cancelled in the compensation of the reverse charging peaks.

Temperature has, however, not only effects on the transducer capacitance, but, instead, acts especially also on the oscillation characteristics of the mechanical structure crucial for the determining and/or monitoring of the process variable. Thus, for example, the stiffness of the material of the oscillatable structure changes with temperature, which, in turn, means a temperature dependence of the resonant frequency, the oscillation amplitude, and the phase shift of the oscillation of the structure existing relative to the excitation signal.

In the case of monitoring a predetermined fill level, this means e.g. that the oscillation frequency occurring in the uncovered, respectively the covered, state of the oscillatable structure is subjected to temperature dependent fluctuations. Correspondingly, there is here, dependent on the temperature, the danger that a switching frequency, set earlier for the measured oscillation frequency for monitoring the exceeding, or subceeding, of the fill level, is not exceeded, or subceeded, in spite of an exceeding, or subceeding, of the predetermined fill level.

The temperature dependence of the oscillation characteristics leads to a marked temperature dependence of the accuracy of measurement of the apparatus.

In order, in spite of this, to assure an as exact as possible and reliable functioning of the apparatus, there is disclosed, for example, in DE 10 2006 007 199 A1 and WO 02/42724 A1, the idea of providing an additional temperature sensor in the region of the transducer, in order to compensate the influence of temperature, and to conduct, e.g. based on the therewith measured temperature, an adapting of the switching frequency.

An additional temperature sensor in the region of the transducer requires, however, space, is connected with additional costs, and must be connected electrically to the electronics of the apparatus, which is, as a rule, arranged removed from the transducer.

SUMMARY OF THE INVENTION

An object of the invention is, consequently, to provide a compact apparatus of the initially named type, which automatically registers the temperature of the transducer.

For this, the invention resides in an apparatus for determining and/or monitoring at least one process variable of a medium in a container, especially a density, a viscosity or a fill level of the medium, and includes:
 a mechanically oscillatable structure, which has at least one oscillation characteristic dependent on the process variable,
 an electromechanical transducer having at least one piezoelectric element,
  which excites the structure, by means of an excitation signal supplied to the transducer, to execute mechanical oscillations, and
  which converts the resulting oscillations of the structure into a received signal, which corresponds to a superpositioning of the excitation signal and a wanted signal representing the oscillation,
 a reference element in parallel with the transducer and supplied with the excitation signal, via which a reference signal independent of the oscillation and corresponding to the excitation signal is tapped, and
 an electronics, which,
  based on the received signal and the reference signal, extracts the wanted signal, and,
  based on the wanted signal, determines and/or monitors the process variable, wherein the electronics includes a temperature measuring device, which supplies the transducer and the reference element, in temperature measurement operation, with an auxiliary signal, whose frequency lies outside a frequency range predetermined by a resonant frequency of the oscillatory structure, and, based on the wanted signal extracted in temperature measurement operation, determines a temperature of the transducer.

In a preferred embodiment, the reference element includes at least one component having an electrically adjustable variable, and there is provided, for adjusting the variable of the component and connected to the temperature measuring device, a control apparatus, which controls the variable of the component to a value, at which a magnitude of an amplitude of the wanted signal in temperature measurement operation is a minimum.

In a further development of this embodiment,
 a memory is provided, in which a characteristic curve of the apparatus is stored, which shows the dependence of the value of the adjustable variable on the temperature of the transducer, and
 temperature is determined based on the controlled value and the characteristic curve.

In a further development, the reference element includes a series circuit of the component having an electrically adjustable variable and a capacitor with a predetermined reference capacitance, and the component is a resistor.

In a first form of embodiment of a first variant of the invention,
 a rectifier is provided, which is fed in temperature measurement operation with the wanted signal,
 the wanted signal rectified by means of the rectifier is fed to a logic unit, especially a microcontroller or a field programmable gate array,
 the logic unit determines an amplitude of the rectified wanted signal and controls the variable of the adjustable component, in temperature measurement operation, to the value, at which the magnitude of the amplitude of the wanted signal is a minimum.

In an embodiment of the first form of embodiment,
the rectifier includes a comparator and a multiplier in parallel with the transducer and connected to the reference element,
the auxiliary signal lies, in temperature measurement operation, parallel to the transducer, on the reference element and on the comparator,
an output signal of the comparator and the wanted signal lie on the multiplier, and
the multiplier is connected to a lowpass filter, whose output signal is applied as rectified, smoothed, wanted signal to the logic unit.

In a second form of embodiment of the first variant of the invention, the apparatus includes
a sampling apparatus for sampling the wanted signal, wherein the sampling apparatus determines the amplitude of the wanted signal in temperature measurement operation for sampling points in time, at which an amplitude of the auxiliary signal has extrema, and,
connected to the sampling apparatus, a logic unit is provided,
which executes a comparison of the sign of the amplitudes of auxiliary signal and wanted signal for sampling points in time, and,
based on the comparison, ascertains a direction and, based on the amplitudes of the wanted signal in temperature measurement operation, a magnitude, by which the value of the variable of the electrical component is to be corrected.

In a further development of the first variant of the invention, there lies on the transducer and the reference element a signal with a periodically continuously variable frequency,
whose periods, in each case, comprise a time span,
in which the frequency of the signal continuously rises or falls, and
in which the signal forms the excitation signal, and
whose periods, in each case, comprise a time interval, in time, leading this time span and/or, in each case, a time interval, in time, following this time span,
in which time interval the frequency of the signal is constant and lies outside of the frequency range predetermined by a resonant frequency of the oscillatory structure, and
in which time interval the signal forms the auxiliary signal.

In an embodiment of the first variant, excitation- and auxiliary signal are both sinusoidal signals, both triangularly shaped signals, both trapezoidally shaped signals, or both rectangular signals.

Additionally, the invention includes a second variant of the apparatus, in the case of which
the excitation signal in temperature measurement operation is a rectangular signal,
the auxiliary signal is a part of the excitation signal, whose frequencies lie above the frequency range predetermined by the resonant frequency of the oscillatory structure,
the temperature measuring device has a highpass filter, which is fed with the wanted signal and which filters out from the wanted signal a measurement signal, whose frequencies above lie the frequency range predetermined by the resonant frequency of the oscillatory structure, and
the temperature measuring device determines temperature of the transducer based on the measurement signal.

Additionally, the invention includes a further development of the apparatus of the second variant, in the case of which
the reference element has at least one component having an electrically adjustable variable, and,
connected to the temperature measuring device, a control apparatus is provided for adjusting the variable of the component, wherein the control apparatus controls the variable of the component to the value, at which the magnitude of the amplitude of the measurement signal in temperature measurement operation is a minimum.

In a further development of the latter further development, a memory is provided, in which a characteristic curve of the apparatus is stored, which shows the dependence of the value of the adjustable variable on the temperature of the transducer, and temperature is determined based on the controlled value and the characteristic curve.

In such case, the reference element includes preferably a series circuit of the component having an electrically adjustable variable and a capacitor with a predetermined reference capacitance, and the component is a compensation resistance.

In a further development, the electronics includes a compensation apparatus, which, based on the temperatures determined in temperature measurement operations, compensates at least one temperature dependence of an oscillation characteristic of the structure dependent on the process variable.

In a further development of an apparatus of the invention for monitoring the exceeding, or subceeding, of a predetermined limit value of the process variable,
for a predetermined temperature range, in which the apparatus is applicable, threshold values for the oscillation characteristic dependent on the process variable are stored in the apparatus, which has the oscillation characteristic upon reaching the limit value at the respective temperature, and
the exceeding or subceeding of the predetermined limit value is monitored based on the temperature ascertained in temperature measurement operation and the threshold value associated with this temperature.

According to the invention, temperature dependence of the transducer capacitance is utilized for determining temperature of the transducer and, therewith, of the mechanically oscillatable structure. In such case, there are exclusively applied, for temperature compensated obtaining of the wanted signal, components of the electronics that are required in any event. Therewith, a reliable temperature measurement is provided, without requirement of additional components for such. A space demanding temperature sensor in the region of the transducer is not required. The apparatus is thereby extremely compact and cost effectively manufacturable.

Based on the measured temperature, it is then possible, over a large temperature range, to execute an exact and reliable determining and/or monitoring of the process variable by performing, based on the measured temperature, a compensation of the temperature dependence of the measured oscillation characteristics dependent on the process variable.

A further advantage of the invention is that, instead of the compensation capacitor used in the state of the art, an adjustable resistor is used, to which a capacitor with predetermined capacitance is connected in series. The predetermined capacitance forms a constant reference capacitance, which is available as a fixed reference point for temperature determination in comparison to the, as a rule, very strongly temperature dependent, transducer capacitance In contrast to the said state of the art, in the case of which some of the examples of embodiments absolutely assume rectangular excitation signals, an option is to operate the apparatus of the invention according to the first variant with different excitation signal forms. Both in the case of an exciting with sinusoidal as well as also with rectangular or trapezoidal voltages, a clean and, above all, temperature independent, wanted signal obtaining and a reliable temperature measurement are assured. In such case, the same apparatus can be operated in normal operation in resonance, be excited with a fixed excitation frequency to forced oscillations, or be operated in the so-called frequency-sweep method with excitation signals of periodically varying frequency. Due to the large number of possible excitation signal forms, the apparatus is applicable in a very universal and versatile way.

BRIEF DESCRIPTION OF THE DRAWINGS

The invention and its advantages will now be explained in greater detail based on the figures of the drawing, in which three examples of embodiments are presented; equal parts are provided in the figures with equal reference characters. The figures of the drawing show as follows.

DETAILED DISCUSSION IN CONJUNCTION WITH THE DRAWINGS

The invention relates to an apparatus for determining and/or monitoring at least one process variable of a medium 1, especially a density, a viscosity or a fill level of the medium in a container 3.

Figure 2:
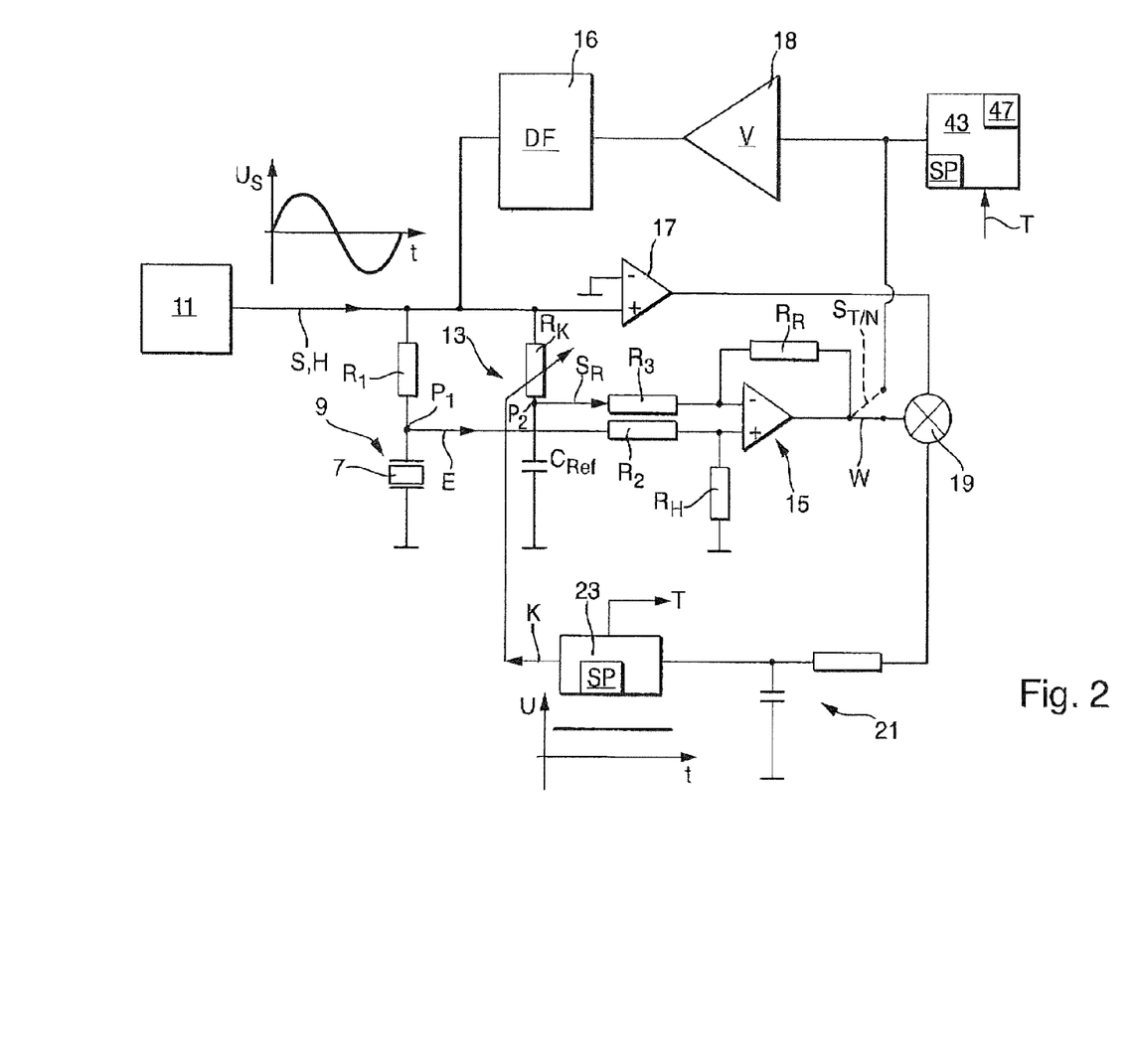
FIG. 2 is a circuit diagram of a first variant of an apparatus of the invention.

FIG. 2 shows a circuit diagram of a first example of an embodiment of an apparatus of the invention. This includes a mechanically oscillatable structure, e.g. the structure 5 shown in FIG. 1, which has at least one oscillation characteristic dependent on the process variable. At least one electromechanical transducer 9 having a piezoelectric element 7 is provided. Electromechanical transducer 9 serves, by means of an excitation signal S supplied to it, to excite the structure 5 to execute mechanical oscillations. In the illustrated example of an embodiment, transducer 9 has a single disc shaped piezoelectric element 7, which is applied, for example, flush against an inner side of the membrane, i.e. the side facing away from the tines of the fork. The piezoelectric element 7 is electrically perceived as a capacitor, whose capacitance is dependent in high measure on temperature T. The piezoelectric element 7 is held between two electrodes, of which one is connected, e.g. via the membrane, to a reference potential, e.g. ground, and of which the other is supplied via a limiting resistor R1 with the excitation signal S.

The excitation signal S is, for example, an alternating voltage, which is produced by means of an excitation signal generator 11 and via which the piezoelectric element 7 is excited to execute thickness oscillations. Accordingly, the therewith connected, mechanically oscillatable structure 5 executes, as a function of the excitation and the process variable, oscillations, which are converted via the transducer 9 into an electrical, received signal E, which corresponds to a superpositioning of the excitation signal S and a wanted signal W representing the oscillation. The received signal E is brought off via a tap P1 located between the transducer 9 and the limiting resistor R1.

Moreover, the apparatus includes a reference element 13 in parallel with the transducer 9 and connected with the excitation signal S. Tapped via the reference element 13 is a reference signal $S_R$, which is independent of the oscillation and corresponds to the excitation signal S.

Reference element 13 is a series circuit of an electrical component, preferably a compensation resistor $R_K$, whose resistance is an electrically adjustable variable, and a capacitor $C_{ref}$, which preferably has a predetermined reference capacitance.

The reference signal $S_R$ is brought off at a tap P2 arranged between the compensation resistor $R_K$ and the capacitor $C_{ref}$.

An electronics is provided, which extracts the wanted signal W based on the received signal E and the reference signal $S_R$. In the case of an optimal matching of the reference element 13 to the transducer 9 supplied in parallel thereto with the excitation signal S via the limiting resistor R1, received signal E and reference signal $S_R$ differ only by the wanted signal W supplementally contained in the received signal E and reflecting the oscillation. Especially, there are, in given cases, disturbance signals equally contained in both signals, such as e.g., charge reversal peaks occurring in connection with rectangular excitation signals. The desired wanted signal W can, consequently, be extracted by forming a simple difference of both signals.

For this, the electronics includes, for example, a difference amplifier 15, whose non inverting input is connected via a limiting resistor R2 with the tap P1 and its inverting input via an additional limiting resistor R3 with the tap P2. Moreover, the non-inverting input is connected via an additional auxiliary resistor $R_A$ to the reference potential. An output signal of the difference amplifier 15 forms the wanted signal W, which is led via a feedback resistor $R_B$ back to the inverting input of the difference amplifier 15.

The electrical capacitance of the transducer 9 is, due to the strong temperature dependence of the capacitances of piezoelectric elements, dependent in high measure on temperature T. This temperature dependence is utilized in temperature measurement operation to determine temperature T of the transducer 9 and, therewith, of the oscillatable structure 5.

For this, a temperature measuring device is provided, which supplies the transducer 9 and the reference element 13, in temperature measurement operation, with an auxiliary signal H, whose frequency f lies outside of a frequency range predetermined by a resonant frequency $f_r$ of the oscillatable structure 5.

For this, two variants will now be described.

In the case of the first variant, the normal operation, in which the apparatus executes the determining and/or monitoring of the process variable, is interrupted for the duration of temperature measurement operation.

If the transducer 9 is applied in normal operation, for example, as frequency determining unit of an oscillatory circuit, in which the wanted signal W is amplified via an amplifier 18 and phase-shifted by means of a phase shifter 16 by a phase shift fulfilling the resonance condition, and fed to the transducer 9 as excitation signal S, then the wanted signal W can be fed here, for example, via an electronically controlled switch $S_{T/N}$ in normal operation to the oscillatory circuit and, in temperature measurement operation, to the temperature measuring device. In this case, the auxiliary signal H, with which the transducer 9 and the reference element 13 are supplied in temperature measurement operation, can be predetermined completely independently of the excitation signal S.

There are applications, in the case of which the excitation signal S in normal operation passes through a predetermined frequency range. In this case, there is fed to the transducer 9 and the reference element 13 preferably a signal with a periodically continuously variable frequency f(t), whose periods, in each case, comprise a time span, in which the frequency of the signal continuously rises, or falls, and, in time, leading this time span and/or, respectively, in time, following this time span, a time interval, in which the frequency $f_H$ of the signal is constant and lies outside of the frequency range predetermined by a resonant frequency $f_r$ of the oscillatory structure. In that case, this signal forms, in the time spans, in which its frequency continuously rises or falls, the excitation signal S, and in the time spans, in which the frequency $f_H$ is constant, the auxiliary signal H. The duration of temperature measurement operation corresponds here to the duration of the latter time spans.

In the case of exciting with the frequency $f_H$ lying outside of the region of the resonant frequency $f_r$, the structure 5 executes a forced oscillation predetermined by the auxiliary signal H. Correspondingly, the received signal E follows the auxiliary signal H, and contains no components dependent on the oscillation characteristics of the structure 5. In the case of an optimal matching of the reference element 13, received signal E and reference signal $S_R$ are, thus, identical, and the wanted signal W disappears. The optimal matching of the reference element 13 occurs—as subsequently explained in detail—by the adjusting of the compensation resistor $R_K$. Due to the temperature dependence of the transducer capacitance, an optimal matching of the reference element 13 achieved in the case of a design temperature $T_R$ is retained, however, only as long as the temperature T of the transducer 9 remains in the region of the design temperature $T_R$.

Figure 3:
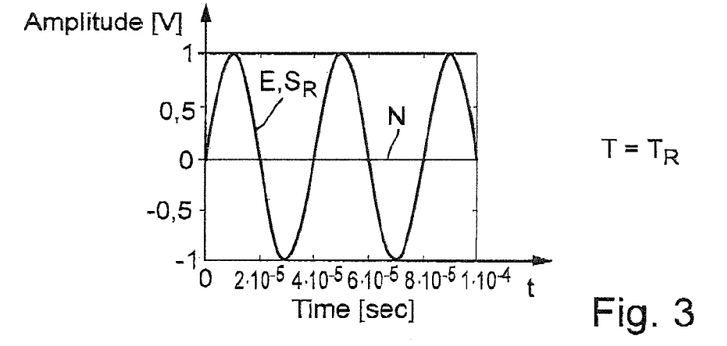
FIG. 3 are amplitudes of the received signal, the reference signal and the wanted signal in temperature measurement operation, in the case of a design temperature, for which an optimal matching of the reference element exists.

FIG. 3 shows received signal E, reference signal $S_R$ and wanted signal W, as they occur in the case of an exciting with a sinusoidal auxiliary signal H, whose frequency f clearly is larger or smaller than the resonant frequency $f_r$ of the apparatus, when temperature T equals the design temperature $T_R$, for which the reference element 13 is optimally matched. As shown in FIG. 3, received signal E and reference signal $S_R$ are identical and have as a function of the time t the same sinusoidal amplitude curve A(E), $A(S_R)$ predetermined by the auxiliary signal H. The amplitude A(W) of the wanted signal W is zero.

Figure 4:
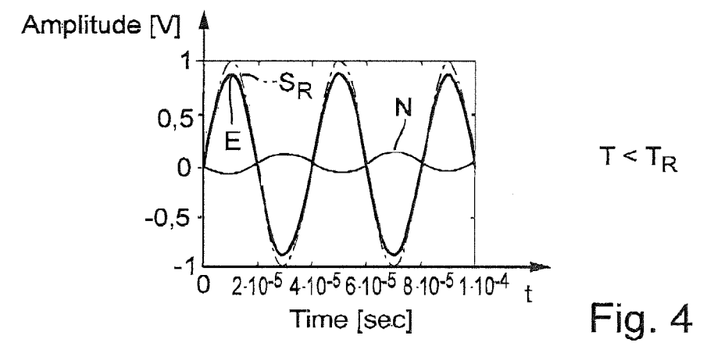
FIG. 4 are amplitudes of the received signal, the reference signal and the wanted signal in temperature measurement operation, in the case of a temperature that lies below the design temperature.

If temperature T sinks to a value below the design temperature $T_R$, then the capacitance of the transducer 9 falls correspondingly. An optimal matching is no longer assured in the case of unchanged reference element 13. FIG. 4 shows received signal E, reference signal $S_R$ and wanted signal W, as they occur in the case of exciting with a sinusoidal auxiliary signal H, whose frequency f is clearly larger or smaller than the resonant frequency $f_r$ of the apparatus, in the case of a temperature T below the design temperature $T_R$. All three signals have here the frequency $f_H$ of the auxiliary signal H. The amplitude A(E) of the received signal E is, however, clearly smaller than the amplitude $A(S_R)$ of the reference signal $S_R$. The wanted signal W generated by the difference forming has correspondingly, relative to the auxiliary signal H (or, equally, relative to the received signal E, or the reference signal $S_R$), a phase shift of 180° and an amplitude A(W) different from zero as a function of the temperature difference between the reigning temperature T and the design temperature $T_R$.

Figure 5:
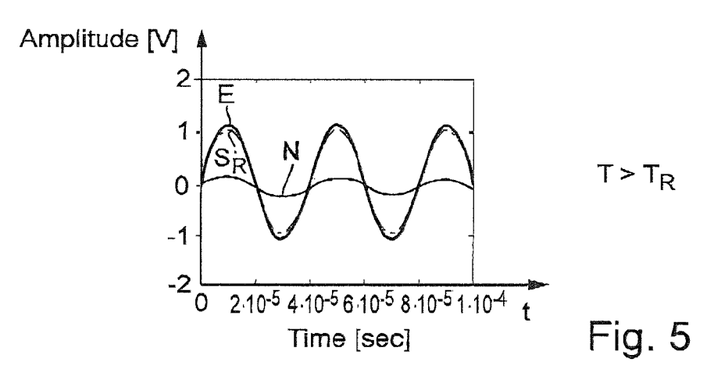
FIG. 5 are amplitudes of the received signal, the reference signal and the wanted signal in temperature measurement operation, in the case of a temperature that lies above the design temperature.

If temperature T rises to a value above the design temperature $T_R$, then the capacitance of the transducer 9 rises correspondingly. An optimal matching is in the case of unchanged reference element 13 also here no longer present. FIG. 5 shows received signal E, reference signal $S_R$ and wanted signal W, as they occur in the case of an exciting with a sinusoidal auxiliary signal H, whose frequency $f_H$ is clearly larger or smaller than the resonant frequency $f_r$ of the apparatus, in the case of a temperature T above the design temperature $T_R$. All three signals have also here the frequency $f_H$ of the auxiliary signal H. The amplitude A(E) of the received signal E is, however, greater than the amplitude $A(S_R)$ of the reference signal $S_R$. The wanted signal W generated by the difference forming has correspondingly, relative to the auxiliary signal H (or, equally, relative to the received signal E, or the reference signal $S_R$), a phase shift of 0° and an amplitude A(W) different from zero as a function of the temperature difference between the reigning temperature T and the design temperature $T_R$.

In the case of a known adjustment of the reference element 13, the amplitude A(W) of the wanted signal W resulting in temperature measurement operation is a direct measure for the capacitance of the transducer 9 and therewith also for its temperature T. Therewith, it is basically possible that the reference element 13 be designed optimally for a predetermined reference temperature, the design temperature of operation, so that, subsequently, based on the amplitudes A(W) of the wanted signal W measured in temperature measurement operation, the temperature T of the transducer 9 can be determined.

Preferably, however, an indirect measuring method is applied, in the case of which, based on the wanted signal W obtained in temperature measurement operation, an optimal matching of the reference element 13 to the instantaneous temperature T of the transducer 9 is performed, and temperature T indirectly derived based on the adjusting of the reference element 13 required for this.

For determining the amplitude A(W) of the wanted signal W, the form of embodiment of temperature measuring device shown in FIG. 2 includes a rectifier fed in temperature measurement operation with the wanted signal W, in order to rectify the wanted signal W. This includes, for example, connected in parallel with the transducer 9 and the reference element 13 and referenced to the reference potential, a comparator 17, which, in temperature measurement operation, is supplied, in parallel with the transducer 9 and the reference element 13, with the auxiliary signal H. The output signal of the comparator 17 and the wanted signal W are applied to a multiplier 19, on whose output the rectified wanted signal W is available. Connected to the multiplier 19 is preferably a lowpass filter 21, which effects a smoothing of the rectified, wanted signal W. The rectified, smoothed, wanted signal is sent to a logic unit 23, especially a microcontroller or a field programmable array (FPGA), which determines the amplitude A(W) of the rectified, smoothed, wanted signal W.

In order, at the same time, to bring about a measuring of temperature T and an optimal matching of the reference element 13, the apparatus includes, connected to the temperature measuring device, a control apparatus for adjusting the variable of the compensation resistor $R_K$. The control apparatus controls the variable of the compensation resistor $R_K$ to the value, in the case of which the magnitude of the amplitude of the wanted signal W, in temperature measurement operation, is a minimum. The control apparatus is preferably contained in the logic unit 23, which has, for this, a control signal output K, via which it controls the variable of the adjustable resistor $R_K$ to the appropriate value.

The set value of the resistor $R_K$ is a measure for temperature T of the transducer 9. The temperature dependence of this value is registered in corresponding characteristic curves determined earlier in a calibration procedure and stored, e.g. in the form a table or a formula, in a storage place, memory SP, associated with the logic unit 23. The logic unit 23 controls, in temperature measurement operation, the value of the resistor $R_K$ as above described, and determines, based on the value controlled to and the associated characteristic curve, the temperature T of the transducer 9.

Figure 6:
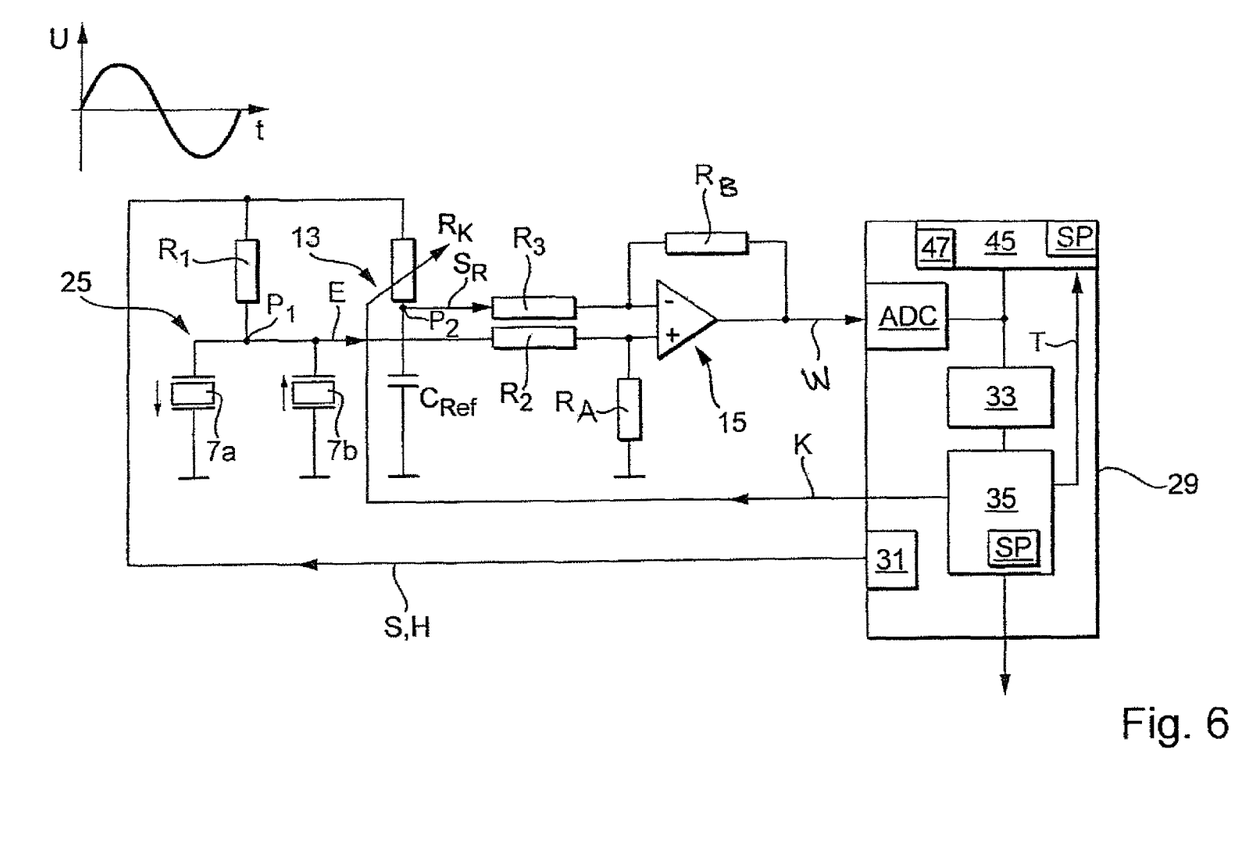
FIG. 6 is a circuit diagram of an additional form of embodiment of the first variant of the apparatus of the invention.

FIG. 6 shows another form of embodiment of the first variant of an apparatus of the invention. The apparatus agrees in large part with the apparatus shown in FIG. 2, so that subsequently only existing differences are explained in greater detail.

One difference is that here, as a further example of a transducer having at least one piezoelectric element, a transducer 25 is provided with two piezoelectric elements 7a, 7b. Such transducers 25 are applied, for example, in connection with the oscillatable structure 27 illustrated in FIG. 7. The structure 27 is a circular, disk shaped membrane, on whose inner side two equally shaped, preferably circular segment shaped, piezoelectric elements 7a and 7b are applied symmetrically about the center of the membrane.

Figure 7:
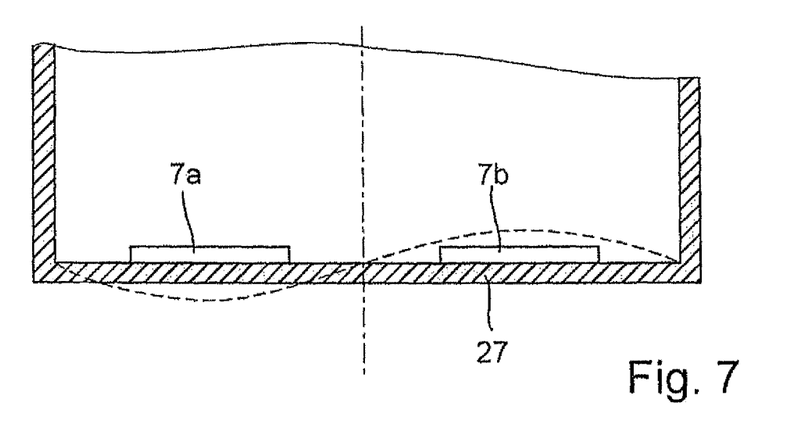
FIG. 7 is a membrane oscillator with two piezoelectric elements applied thereon.

Transducer 25 serves, also here, both as producer as well as also as receiver of the mechanical oscillations of the mechanically oscillatable structure 27. For this, both piezoelectric elements 7a and 7b are operated electrically in parallel and with the same excitation signal S, or supplied the same auxiliary signal H. In the case of opposite polarization of the elements 7a, 7b, the membrane is thereby excited to—here indicated by a dashed line—oscillations of the second mode.

The received signal E of the transducer 25, the reference signal $S_R$ and the wanted signal W are derived in the manner already described based on FIG. 2.

In contrast to the apparatus illustrated in FIG. 2, the apparatus shown here includes a temperature measuring device and a control system for control of the compensation resistor $R_K$, which are embodied as integral components of an electronic unit 29, e.g. a microcontroller or a field programmable gate array (FPGA).

Moreover, this unit 29 preferably includes an integrated signal generator 31, which, in normal operation, generates the excitation signal S and, in temperature measurement operation, the auxiliary signal H, with which both the transducer 25 as well as also the reference element 13 are supplied in parallel.

The wanted signal W is fed in digital form to the unit 29 via an analog-digital converter ADC. Unit 29 includes a sampling apparatus 33 for sampling the wanted signal W. Since the wanted signal W, in temperature measurement operation, has relative to the auxiliary signal H a phase shift of 0°, or 180°, it suffices to determine the amplitude A(W) of the wanted signal W, in temperature measurement operation, at sampling points in time, at which the amplitude of the auxiliary signal H has extrema.

If the auxiliary signal H is, in such case, generated by the unit 29, the time reference of both signals required for this is given automatically.

Alternatively, production of the excitation signal S and the auxiliary signal H could here naturally occur in manner equal to that shown for the example of an embodiment illustrated in FIG. 2. In that case, the wanted signal W would be sampled either more exactly, or the time reference required for the above described, extremely efficient sampling would be produced in some other manner. For producing the time reference, e.g. the phase relationship of the auxiliary signal H can be ascertained by leading the auxiliary signal H —, as also in FIG. 2—in parallel through a comparator 17, and performing a sampling of its output signal.

Unit 29 includes, connected to the sampling apparatus 33, a logic unit 35, which, in temperature measurement operation, executes a comparison of the sign of amplitudes of auxiliary signal H and wanted signal W for sampling points in time, and, based on the comparison, ascertains a direction and, based on amplitudes of the wanted signal W, in temperature measurement operation, a magnitude, by which the value of the variable of the compensation resistor $R_K$ is to be corrected. The control is performed via a control output K of the unit 29 connected to the logic unit 35.

Exactly as in the case of the earlier described example of an embodiment, the set value of the resistor $R_K$ is also here a measure for temperature T of the transducer 25. The temperature dependence of this value is registered in corresponding characteristic curves earlier determined in a calibration procedure and stored in a memory SP associated with the logic unit 35. The logic unit 35, in temperature measurement operation, controls the value of the resistor $R_K$, and determines, based on the value controlled to and the associated characteristic curve, the temperature T of the transducer 25.

Besides the first variant described based on FIGS. 2 and 6, in the case of which normal operation is interrupted for temperature measurement, the invention includes a second variant, with which temperature measurement can be executed during the normal operation of the apparatus.

Figure 8:
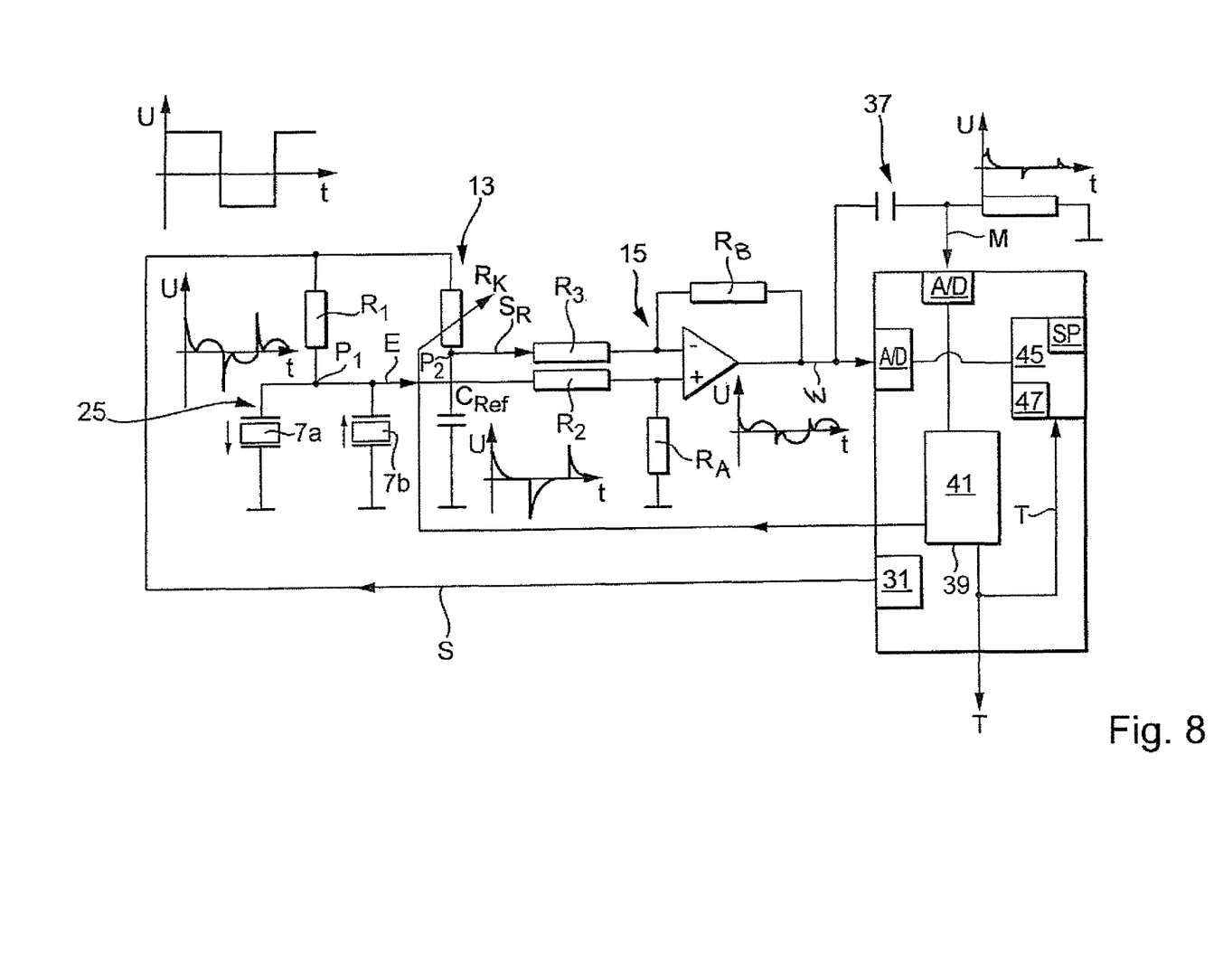
FIG. 8 is a circuit diagram of a second variant of the apparatus of the invention.

FIG. 8 shows a circuit diagram of an example of an embodiment for this. Due to the large agreement with the form of embodiment of the first variant illustrated in FIG. 6, only differences will be explained in greater detail.

Temperature measurement occurs also in the case of the second variant via a temperature measuring device, which supplies the transducer 25 and the reference element 13, in temperature measurement operation, with an auxiliary signal H, whose frequencies lie outside of the frequency range predetermined by the resonant frequency $f_r$ of the oscillatable structure 27.

In order to be able to execute the matching of the reference element 13 and the measuring temperature T of the transducer 25 during normal operation of the apparatus, in the case of this second variant, at least in temperature measurement operation, an excitation signal $S_H$ is applied that contains the auxiliary signal H.

In this way, it is possible to operate the apparatus permanently at the same time in normal operation and in temperature measurement operation. Alternatively, naturally also parallel operation intervals can be provided, in which temperature measurement operation is executed, sporadically, periodically or at predetermined times, in parallel with normal operation. In this case, the excitation signal S needs only to contain the auxiliary signal H during the parallel operation, while, in the purely normal operation, it is freely selectable, exactly as in the case of the first variant.

According to the invention, the excitation signal $S_H$ applied in parallel operation is a rectangular signal, especially a rectangularly alternating voltage. Rectangular signals have, due to their signal form, besides their fundamental frequency, unavoidable, higher frequency fractions, whose frequencies lie above the resonant frequency $f_r$ of the mechanically oscillatable structure 27. These higher frequency fractions of the excitation signal $S_H$ form the auxiliary signal H.

In contrast to the sinusoidal excitation-, respectively auxiliary, signals S; H illustrated in FIGS. 2 to 6, the rectangular excitation signal $S_H$ applied in the second variant, unavoidably containing the auxiliary signal H, brings about the initially already described, charge reversal currents across the transducer 25 and the reference element 13. This is reflected in the received signal E and in the reference signal $S_R$ as charge reversal peaks.

Also here, completely analogously to the previous examples of embodiments, the signal components of received signal E and reference signal $S_R$ attributable to the auxiliary signal H, in the case of an optimal matching of the reference element 13, cancel one another in the forming of the wanted signal W. If temperature T changes relative to the design temperature $T_R$, for which the reference element 13 was last optimally matched, then there arises, due to the change of the capacitance of the transducer 25 connected with the change of temperature, a detuning between the measurement branch containing the transducer 25 and the reference branch formed by the reference element 13. This leads to the fact that the wanted signal W has besides the signal portion representing the mechanical oscillation also a signal portion attributable to the auxiliary signal H.

In contrast to the signal portion representing the oscillation, the signal portion of the wanted signal W attributed to the auxiliary signal H has, however, exclusively frequencies, which lie above the frequency range predetermined by the resonant frequency $f_r$ of the oscillatable structure 27.

Correspondingly, the temperature measuring device includes, in the case of this variant, fed with the wanted signal W, a highpass filter 37, which filters out from the wanted signal W a measurement signal M, whose frequencies lie above the frequency range predetermined by the resonant frequency $f_r$ of the oscillatable structure 27.

Also here, temperature of the transducer 25 can, in the case of known adjustment of the reference element 13, be directly determined based on the measurement signal M. Preferably, however, also here, the indirect way is chosen, using the matching of the reference element 13.

For this, the measurement signal M is fed, via an analog-digital converter A/D, to a logic unit 39 preferably integrated in the electronic unit 29. Logic unit 39 includes a control apparatus 41 for adjusting the variable of the component $R_K$, and controls the variable of the component $R_K$ to the value, in the case of which the magnitude of the amplitude of the measurement signal M is, in temperature measurement operation, a minimum.

Analogously to the explanations for FIGS. 3 to 5, also here, the amplitudes A of the fractions of the received signal E attributable to the auxiliary signal H are smaller than the amplitudes A of the fractions of the reference signal $S_R$ attributable to the auxiliary signal H, when temperature T sinks to values, which lie below the design temperature $T_R$, for which the reference element 13 is optimally matched, and vice versa.

Correspondingly, in the logic unit 39, for example, a mean amplitude $A_M$ of the measurement signal M and its sign are determined. The mean amplitude $A_M$ of the measurement signal M delivers the magnitude and sign of the direction, by which the value of the variable of the compensation resistor $R_K$ is to be corrected. The control is also here preferably performed via a control output of the unit 29 connected to the control apparatus 41.

Logic unit 39 determines temperature T in the manner already described above in connection with the apparatuses according to the first variant.

The apparatuses of the invention have the advantage that, in temperature measurement operation, simultaneously, an optimal matching of the reference element 13 and the measuring of temperature T are performed. Therewith, in the following normal operation, a wanted signal W is available, which is compensated as regards temperature dependence of the capacitance of the one or more applied transducers 9, 25.

The wanted signal W is fed to a measuring- and evaluating unit, which, based on the wanted signal W, determines and/or monitors the process variable. In the example of an embodiment illustrated in FIG. 2, a measuring- and evaluating unit 43 is provided, which is fed the analog wanted signal W. In the examples of embodiments illustrated in FIGS. 6 and 8, a measuring- and evaluating unit 45 integrated in the unit 29 is provided, which is fed the wanted signal W in digital form.

For determining and/or monitoring the process variable, operating- and evaluation methods known from the state of the art can be applied. In such case, the measuring- and evaluation circuit 43, 45 derives, based on the wanted signal W, an oscillation characteristic of the mechanically oscillatable structure 5, 27 dependent on the particular process variable to be determined and/or monitored, e.g. the fill level, the density or the viscosity. Counted among the oscillation characteristics are especially the oscillation frequency, the oscillation amplitude and/or the phase shift of the oscillation relative to the excitation signal S, which are metrologically registerable, respectively, based on the frequency of the wanted signal W, the amplitude of the wanted signal W, or the phase shift of the wanted signal W relative to the excitation signal S.

The oscillation characteristics of the oscillatable structure 5, 27 have, besides their dependence on the process variable, also a temperature dependence. The main cause for this is that the stiffness of the material of the oscillatable structure 5, 27 changes with temperature. Accordingly, the oscillation characteristics of the structure 5, 27, especially the oscillation frequency, the oscillation amplitude and/or the phase shift of the oscillation relative to the excitation signal S, have a temperature dependence. The temperature dependences of these oscillation characteristics are determined in a calibration procedure and stored, for example, in the form of characteristic curves, in a memory SP associated with the measuring- and evaluating system 43, 45.

The measuring- and evaluating system 43, 45 includes a compensation apparatus 47, which, based on the characteristic curves and the temperatures T determined in temperature measurement operations, compensates the temperature dependence of the particular oscillation characteristic of the structure 5, 27 used for determining and/or monitoring the desired process variable.

In the case of an apparatus of the invention for monitoring exceeding or subceeding of a predetermined limit value of a process variable, e.g. a predetermined fill level, this occurs, for example, by determining for the oscillation characteristic dependent on the process variable, in a calibration procedure for a predetermined temperature range, threshold values, which the oscillation characteristic has, upon reaching the limit value at the respective temperature T. The threshold values are stored as a function of temperature in the apparatus in the memory SP associated with the measuring- and evaluating system 43, 45.

The actual monitoring is done by the measuring- and evaluating system 43, 45, which, based on the temperature ascertained in temperature measurement operation T, reads out the threshold value associated with this temperature T, and based on this threshold value, monitors the exceeding, or subceeding, of the predetermined limit value.

The invention claimed is:

1. An apparatus for determining and/or monitoring at least a density, a viscosity or a fill level of a medium in a container, comprising:
   a mechanically oscillatable structure, which has at least one oscillation characteristic dependent on the density, viscosity or fill level;
   an electromechanical transducer having at least one piezoelectric element, which excites said mechanically oscillatable structure, by means of an excitation signal supplied to said electromechanical transducer, to execute mechanical oscillations, and which converts the resulting oscillations of said mechanically oscillatable structure into a received signal, which corresponds to a superpositioning of the excitation signal and a wanted signal representing the oscillation;
   a reference element in parallel with said electromechanical transducer and supplied with the excitation signal, via which a reference signal independent of the oscillation and corresponding to the excitation signal is tapped, said reference element comprising a series circuit of at least a compensation resistor having an electrically adjustable variable and a capacitor with a predetermined reference capacitance, wherein a control apparatus is provided for adjusting the variable of said compensation resistor and connected to the temperature measuring device, which controls the variable of said compensation resistor to a value, at which a magnitude of an amplitude of the wanted signal in temperature measurement operation is a minimum; and
   an electronics, which, based on the received signal and the reference signal, extracts the wanted signal, and based on the wanted signal, determines and/or monitors the density, viscosity or fill level, wherein:
   said electronics includes a temperature measuring device, which supplies said electromechanical transducer and said reference element, in temperature measurement operation, with an auxiliary signal, whose frequency lies outside a frequency range predetermined by a resonant frequency of said mechanically oscillatable structure, and, based on the wanted signal extracted in temperature measurement operation, determines a temperature of said electromechanical transducer.

2. The apparatus as claimed in claim 1, further comprising:
   a memory, in which a characteristic curve of the apparatus is stored, which shows the dependence of the value of the adjustable variable on the temperature of said electromechanical transducer, and wherein:
   temperature is determined based on the controlled value and the characteristic curve.

3. The apparatus as claimed in claim 1, further comprising:
   a rectifier, which is fed in temperature measurement operation with the wanted signal, wherein:
   the wanted signal rectified by means of said rectifier is fed to a logic unit, especially a microcontroller or a field programmable gate array; and
   said logic unit determines an amplitude of the rectified wanted signal, and controls the variable of said adjustable component, in temperature measurement operation, to the value, at which the magnitude of the amplitude of the wanted signal is a minimum.

4. The apparatus as claimed in claim 3, wherein:
   said rectifier includes a comparator and a multiplier in parallel with said mechanically oscillatable structure and connected to said reference element;
   the auxiliary signal lies, in temperature measurement operation, parallel on said mechanically oscillatable structure, on said reference element and on said comparator;
   an output signal of said comparator and the wanted signal lie on said multiplier; and
   said multiplier is connected to a lowpass filter, whose output signal is applied as rectified, smoothed, wanted signal to said logic unit.

5. The apparatus as claimed in claim 1, further comprising:
   a sampling apparatus for sampling said wanted signal, wherein:
   said sampling apparatus determines the amplitude of said wanted signal in temperature measurement operation for sampling points in time, at which an amplitude of the auxiliary signal has extrema, and connected to said sampling apparatus, a logic unit is provided, which executes a comparison of the sign of amplitudes of said auxiliary signal and said wanted signal for sampling points in time; and
   based on the comparison, ascertains a direction and, based on amplitudes of said wanted signal in temperature measurement operation, a magnitude, by which the value of the variable of said compensation resistor is to be corrected.

6. The apparatus as claimed in claim 1, wherein:
   there lies on said electromechanical transducer and said reference element a signal with a periodically continuously variable frequency, whose periods, in each case, comprise a time span, in which the frequency of the signal continuously rises or falls, and in which the signal forms said excitation signal, and
   whose periods, in each case, comprise a time interval, in time, leading this time span, and/or, in each case, a time interval, in time, following this time span;
   in which time interval the frequency of the signal is constant and lies outside of the frequency range predetermined by a resonant frequency of said mechanically oscillatable structure; and
   in which time interval the signal forms said auxiliary signal.

7. The apparatus as claimed in claim 1, wherein:

said excitation- and auxiliary signal, are: both sinusoidal signals, both trapezoidally shaped signals, both triangularly shaped signals, or both rectangular signals.

8. The apparatus as claimed in a claim 1, wherein:

said excitation signal in temperature measurement operation is a rectangular signal;

said auxiliary signal is a part of said excitation signal, whose frequencies lie above the frequency range predetermined by the resonant frequency of said oscillatable structure;

said temperature measuring device has a highpass filter, which is fed with said wanted signal and which filters out from said wanted signal a measurement signal, whose frequencies lie above the frequency range predetermined by the resonant frequency of said mechanically oscillatable structure; and said temperature measuring device determines temperature of said electromechanical transducer based on the measurement signal.

9. The apparatus as claimed in claim 8, wherein:

said reference element has at least one component having an electrically adjustable variable; and connected to the temperature measuring device, a control apparatus is provided for adjusting the variable of said at least one component, said control apparatus controls the variable of said at least one component to the value, at which the magnitude of the amplitude of said measurement signal in temperature measurement operation is a minimum.

10. The apparatus as claimed in claim 9, further comprising:

a memory, in which a characteristic curve of the apparatus is stored, which shows the dependence of the value of the adjustable variable on temperature of said electromechanical transducer, wherein:

temperature is determined based on the controlled value and the characteristic curve.

11. The apparatus as claimed in claim 9, wherein:

said reference element includes a series circuit of said at least one component having an electrically adjustable variable and a capacitor with a predetermined reference capacitance; and said component is a compensation resistance.

12. The apparatus as claimed in claim 1, wherein:

said electronics includes a compensation apparatus, which, based on the temperatures determined in temperature measurement operations, compensated at least one temperature dependence of an oscillation characteristic of said mechanically oscillatable structure dependent on the density, viscosity or fill level.

13. The apparatus as claimed in claim 1, wherein:

the apparatus monitors an exceeding, or subceeding, of a predetermined limit value of the density, viscosity or fill level, for a predetermined temperature range, in which the apparatus is applicable, threshold values for the oscillation characteristic dependent on the density, viscosity or fill level are stored in the apparatus, which has the oscillation characteristic upon reaching the limit value at the respective temperature, and the exceeding, or subceeding, of the predetermined limit value is monitored based on the temperature ascertained in temperature measurement operation and the threshold value associated with this temperature.

\* \* \* \* \*